United States Patent [19]

Chung et al.

[11] Patent Number: 5,731,007
[45] Date of Patent: Mar. 24, 1998

[54] PHARMACEUTICAL COMPOSITION FOR SKIN DISEASES

[75] Inventors: Kae Jong Chung; Man Sik Chang, both of Seoul; Jong Ok Chun; Jae Kwang Chun, both of Kyunggi-do; Wahn Soo Choi, Seoul; Sung Chul Kim, Kyunggi-do, all of Rep. of Korea

[73] Assignee: Yungjin Pharmaceutical Co., Ltd., Seoul, Rep. of Korea

[21] Appl. No.: 647,961

[22] PCT Filed: Mar. 23, 1995

[86] PCT No.: PCT/KR95/00025

§ 371 Date: Jul. 25, 1996

§ 102(e) Date: Jul. 25, 1996

[87] PCT Pub. No.: WO95/25523

PCT Pub. Date: Sep. 28, 1995

[30] Foreign Application Priority Data

Mar. 23, 1994 [KR] Rep. of Korea ............... 94-5839

[51] Int. Cl.$^6$ .................. A61K 35/14; A61K 35/16; A61K 35/18
[52] U.S. Cl. .................. 424/529; 424/530; 424/531; 424/532; 424/533; 424/534; 514/40
[58] Field of Search ............... 424/529, 530, 424/531, 532, 533, 534; 514/40

[56] References Cited

U.S. PATENT DOCUMENTS

| | | |
|---|---|---|
| 3,293,836 | 12/1966 | Heth. |
| 3,932,618 | 1/1976 | Fujii et al.. |
| 4,177,261 | 12/1979 | Dietze et al.. |
| 5,290,555 | 3/1994 | Guthauser et al. .......... 424/401 |

OTHER PUBLICATIONS

Budarari et al. "The Merck Index" (11th Ed.), Merck and Co., Inc., Rahway, NJ. (1989), pp. 972–973.

*Primary Examiner*—Marianne M. Cintins
*Assistant Examiner*—M. Moezie
*Attorney, Agent, or Firm*—Finnegan Henderson Farabow Garrett and Dunner

[57] ABSTRACT

The present invention relates to novel pharmaceutical composition for skin diseases, in particular to novel pharmaceutical composition useful for treatment of skin diseases; e.g. burns, wounds, general operative wounds, pernio, decubitus, folliculitis, impetigo, intertrigo, radiation ulcer, acne vulgaris or infectious eczematous dermatitis comprising deproteinized dialysate of calf's blood with tissue regenerative activity and aminoglycoside antibiotic with bacterial infection inhibitory activity as active ingredients.

5 Claims, No Drawings

PHARMACEUTICAL COMPOSITION FOR SKIN DISEASES

FIELD OF THE INVENTION

The present invention relates to novel pharmaceutical composition for skin diseases, in particular which comprises deproteinized dialysate of calf's blood and aminoglycoside antibiotic as active ingredients.

BACKGROUND OF THE INVENTION

It is known that skin diseases, e.g. burns, wounds, general operative wounds, pernio, decubitus, folliculitis, impetigo, intertrigo, radiation ulcer, acne vulgaris or infectious eczematous dermatitis develop erythema, swelling, bulla, erosion, or ulcer etc., being accompanied with bacterial infections.

For the treatement of those skin diseases, tissue regeneration activators which can accelerate regeneration of the necrotinized tissue and fibroblast proliferation have been developed [Acta. Therapeutica Vol. 10,107–115 (1984)]. However, it has been pointed out as demerits that those activators are unable to prevent appropriately bacterial infections in foci during the treatment.

In addition, topical dosage forms containing antibiotics and being formulated with proper skin protecting bases have been developed for the same purpose [Journal of Antimicrobial Chemotherapy Vol. 16, 519–526(1985)]. Those formulations could partially achieve preventing bacterial infections in foci, but they could not achieve the most preferable treatments due to lack of the ability to accelerate regeneration of the necrotinized tissue and fibroblast proliferation.

SUMMARY OF THE INVENTION

The present inventors fixed eye on the possibility that if the two drugs with different mechanisms of action are combined to formulate a dosage form from which the dissolutions of the two ingredient are superior to those of the same ingredients from the conventional ointment or cream used for treatment of skin diseases, such as burns, having potential to be infected with bacteria, synergism of the two drugs can normalize skin function more effectively. Then the present inventors have carried out extensive research to develop a useful pharmaceutical composition which accelerate tissue regeneration and at the same time have antibacterial activity for treatment of skin diseases; and as a result, have discovered the excellent treatment of the diseases and decrease of the expression of acute skin diseases are obtained when deproteinized dialysate of calf's blood and aminoglycoside antibiotic were combined to treat skin diseases. The deproteinized dialysate of calf's blood has the ability to accelerate tissue regeneration, and the antibiotic has antimicrobial activity and the deproteinized dialysate of calf's blood in combination of antibiotic also compensates the demerits of each component.

Accordingly, it is an object of the present invention to provide novel pharmaceutical composition useful for treatment of skin diseases, which can give an immediate therapeutic effects through the well-marked tissue regenerative action and the effective antibacterial action, and shorten therapeutic period.

DETAILED DESCRIPTION OF THE INVENTION

The present invention is to provide a novel pharmaceutical composition useful for treatment of skin diseases comprising deproteinized dialysate of calf's blood and aminoglycoside antibiotic as active ingredients.

Deproteinized dialysate of calf's blood, tissue regenerative component of the composition of the present invention, is protein-free haemodialysate obtained by drawing the blood from the reticuloendothelial system of the fully grown young calf regenerated by the special organ extraction method and then removing protein completely through dialysis. The deproteinized dialysate of calf's blood is sold in the trademark of Solcoseryl® (Solco Basle Ltd., Swiss). It is known that the said deproteinized dialysate of calf's blood includes organic compounds, such as amino acid, ketonic acid, oxy acids, deoxy ribosides, purines, and unknown polypeptide, etc., and inorganic compounds, such as Na, K, Ca, Fe, Co, P, Chloride, and N, to increase utilization of oxygen in cells and to accelerate regeneration of the necrotinized tissue and formation of fibroblast tissue & epitherial tissue [Arzneim-Forsch (Drug Res.) Vol. 15, 750–754 (1965); VASA Band Vol. 2, 81–83 (1973)].

Aminoglycoside antibiotic, bacterial infection inhibitory component of the s composition of the present invention, may include neomycin sulfate, gentamicin sulfate, micronomicin sulfate, amikacin sulfate, kanamycin sulfate, tobramycin sulfate, netilmicin sulfate, dibekacin sulfate, sisomicin sulfate, or astromicin sulfate and more preferred is micronomicin sulfate.

Micronomicin sulfate is an aminoglycoside antibiotic with a wide antibacterial spectrum against both gram positive and negative bacteria such as *Staphylococcus, Pseudomonas aeruginosa, Proteus, Serratia, Escherichia coli, Klebsiella pneumoniae, Enterobacter*, etc., and has an effective bacteriocidal activity against infections by strains resistant to various antibiotics such as kanamycin, and has less side effects relatively [Chemotherapy Vol. 25, 1844–1850 (1977);Chemotherapy Vol. 25, 1943–1951 (1977)].

In accordance with the present invention, the therapeutic effects produced by the administration of the deproteinized dialysate of calf's blood in combination with aminoglycoside antibiotics are more potent than those by the administration of each component independently. Especially, the control of the amount of components in the pharmaceutical composition of the present invention may balance fibroblast proliferation and epitherial tissue formation, during the acceleration of tissue regeneration, to minimize scars.

In accordance with the present invention, it is preferred that the contents of the deproteinized dialysate of calf's blood and the aminoglycoside antibiotic are 1~30 w/w % and 0.1~2 w/w % to total composition, respectively. More preferred is that the contents of the deproteinized dialysate of calf's blood and the aminoglycoside antibiotic are 5~20 w/w % and 0.3~1 w/w % to total composition, respectively.

The pharmaceutical composition of the present invention may contain one or more pharmaceutically acceptable carriers such as base, stabilizer, emulsifier to increase the stability of the said composition, and to be formulated into gel, gel-cream, or topical liquid solution.

The pharmaceutical composition of the present invention may contain poloxamer, sodium carboxymethylcellulose, or carbomer as base, sodium chloride or sodium hydroxide as stabilizer, W/O surfactant such as cetearyl octanoate, O/W surfactant or mixture thereof as emulsifier, propylene glycol or glycerin as humectant.

The pharmaceutical composition of the present invention may be formulated into gel containing 18~22 w/w % of poloxamer, 1~5 w/w % of propylene glycol, and 0.5~3 w/w % of sodium chloride.

The pharmaceutical composition of the present invention may be formulated into gel-cream containing 18~22 w/w % of poloxamer, 1~5 w/w % of propylene glycol, and 5~15 w/w % of cetearyl octanoate.

The pharmaceutical composition of the present invention may be formulated into topical liquid solution containing 5~15 w/w % of propylene glycol.

However, the amount of the above carriers in the pharmaceutical composition of the present invention may be changed depending on dissolution rate and appearance of micronomicin sulfate.

The pharmaceutical composition of the present invention may be applied to the focus of skin disease, 1~2 times per day in the conventional topical dosage forms.

In order to prove the superior activity of the pharmaceutical composition of the present invention, the present inventors carried out long term study to define the ratio of components, and then the optimized ratio may be applied to make the pharmaceutical composition that cures more effectively skin diseases such as wound.

Especially, the present inventors carried out tissue regeneration study and topical antibacterial activity study by changing the ratio of component of the composition of the present invention. The present inventors utilized or modified the animal model [YAKUZAIGAKU Vol. 53, No. 3, 185~190(1993)] to carry out the tissue regeneration study, and the animal model [Antimicrobial Agents and Chemotherapy Vol. 10, No. 1,38~44(1976)] to carry out the topical antibacterial activity study.

As a result, groups treated with the deproteinized dialysate of calf's blood in combination with micronomicin sulfate showed better results in the tissue regeneration and the topical antibacterial activity than groups treated with the deproteinized dialysate of calf's blood or micronomicin sulfate alone showed. It proves that the pharmaceutical composition of the present invention comprising deproteinized dialysate of calf's blood and micronomicin sulfate possesses more potent activity than those of the simple mixture. Therefore, those experiments showed that the pharmaceutical composition of the present invention accelerates regeneration of skin tissue, and has prompt therapeutic effect. In addition, the pharmaceutical composition of the present invention can decrease the therapeutic period.

The present inventors carried out experiments for pharmaceutical incompatibility among components in the composition and stability test on ageing. The results showed that the components of the pharmaceutical composition of the present invention had no pharmaceutical incompatibility, and was stable during storage for a long time.

The following Examples are provided for the purposes of illustrating certain aspects of the present invention only; and are not to be construed as limiting the scope of the present invention in any way.

The terms and abbreviations used in the instant Examples have their normal meaning unless otherwise designated, for example, "C" refers to degrees celsius; "g" refers to gram; "ml" means milliliter.

TEST EXAMPLE 1

Tissue regeneration activity study

Wounds were produced on the backs of male ICR mice (1 cm in diameter).

The open wounds were topically treated with the pharmaceutical compositions twice a day for 2 weeks.

The dose is 0.3 g/wound unless otherwise designated. The results of tissue regeneration activity test according to the compositions are shown in table 1.

TABLE 1

| Test Group | The compositions(w/w %) | | | $CT_{50}(day)^{(2)}$ |
| --- | --- | --- | --- | --- |
|  | MCR[5] | Solcoseryl[1] | No. of mice | mean ± S.D. |
| Control | — | — | 10 | 9.03 ± 0.26 |
| Base only[3] | — | — | 10 | 8.46 ± 0.09 |
| 1 | — | 10 | 10 | 7.92 ± 0.17 |
| 2 | 0.50 | — | 10 | 7.97 ± 0.12 |
| 3 | 0.50 | 5 | 10 | 7.46 ± 0.44 |
| 4 | 0.50 | 10 | 10 | 7.23 ± 0.23[4] |
| 5 | 0.50 | 20 | 10 | 7.37 ± 0.31 |

[1]The deproteinized dialysate of calf's blood, Solco Basle Ltd. Swiss
[2]The time for curing 50% of wound by area (mean ± standard deviation)
[3]Treated only with vehicle
[4]$P < 0.05$ against group 1 by Student t-test
[5]Micronomicin sulfate Table 1 shows the pharmaceutical compositions containing both the deproteinized dialysate of calf's blood and micronomicin sulfate possess more potent activities for curing wound than those of the deproteinized dialysate of calf's blood or micronomicin sulfate alone. Especially, the group 4 exhibits superior therapeutic effect with significance compared with that of the group 1, while the group 5 did not show significant therapeutic effect compared with that of group 1.

It suggests that these results are caused by unbalanced fibroblast proliferation and the formation of epitherial tissue.

As a result, therapeutic effect can be obtained when the combination of the deproteinized dialysate of calf's blood (5~20 w/w%) and micronomicin sulfate (0.5 w/w %) is used. Especially, the pharmaceutical composition comprising 10 w/w % of deproteinized dialysate of calf's blood and 0.5 w/w % of micronomicin sulfate exhibits the most potent therapeutic effect.

TEST EXAMPLE 2

Topical antibacterial activity study

Wounds were produced on the backs of male ICR mice (1 cm in diameter).

Each group consisted of 10 mice. The wound was treated with $1 \times 10^4$ CFU (Colony Forming Unit) of *Staphylococcus aureus*. One day after direct infections the wounds were treated with the pharmaceutical composition of the present invention topically twice a day for 2 weeks. The CFU of the wounds were counted before and after administration of the composition of the present invention. The dose is 0.3g/wound unless otherwise designated. The results of topical antibacterial activity test with the compositions are shown in table 2.

TABLE 2

| Group | Compositions (w/w %) MCR[1] | Compositions (w/w %) Solcoseryl | No. of mice | mean CFU/wound before administration | after administration (day) 1 | 6 | 9 | 14 |
|---|---|---|---|---|---|---|---|---|
| Control | — | — | 10 | $6.5 \times 10^5$ | $2.6 \times 10^6$ | $7.6 \times 10^7$ | $3.7 \times 10^7$ | $3.8 \times 10^6$ |
| base only[2] | — | — | 10 | $6.5 \times 10^5$ | $3.8 \times 10^5$ | $4.4 \times 10^6$ | $4.7 \times 107$ | $2.7 \times 10^6$ |
| 1 | — | 10 | 10 | $6.5 \times 10^5$ | $3.8 \times 10^5$ | $4.5 \times 10^7$ | $1.4 \times 10^7$ | $7.1 \times 10^5$ |
| 2 | 0.50 | — | 10 | $6.5 \times 10^5$ | $9.0 \times 10^4$ | $3.2 \times 10^6$ | $3.4 \times 10^6$ | $6.0 \times 10^4$ |
| 3 | 0.25 | 10 | 10 | $6.5 \times 10^5$ | $3.6 \times 10^5$ | $2.9 \times 10^6$ | $5.2 \times 10^5$ | $2.0 \times 10^4$ |
| 4 | 0.50 | 10 | 10 | $6.5 \times 10^5$ | $8.0 \times 10^4$ | $6.3 \times 10^5$ | $1.8 \times 10^6$ | $6.0 \times 10^3$ |
| 5 | 1.00 | 20 | 10 | $6.5 \times 10^5$ | $9.0 \times 10^4$ | $2.6 \times 10^5$ | $2.3 \times 10^5$ | $3.0 \times 10^3$ |

[1]Micronomicin sulfate
[2]Treated only with vehicle

Table 2 shows the pharmaceutical compositions containing both the deproteinized dialysate of calf's blood and micronomicin sulfate possess more potent activities than the deproteinized dialysate of calf's blood or micronomicin sulfate alone in topical antibacterial activity, too. These excellent therapeutic effects are caused by both increasing tissue regeneration activity and decreasing bacterial infection in wound. As a result, the pharmaceutical composition of the present invention could have prompt therapeutic effects and decrease the therapeutic period by accelerating tissue repair.

EXAMPLE 1

| Gel | |
|---|---|
| Micronomicin sulfate | 0.5 g |
| Solcoseryl | 5.0 g |
| Poloxamer | 18.0 g |
| Propylene glycol | 3.0 g |
| Sodium chloride | 0.9 g |
| Methyl p-hydroxybenzoate | 0.18 g |
| Propyl p-hydroxybenzoate | 0.02 g |
| Purified water | q.s. |

Micronomicin sulfate, Solcoseryl, and sodium chloride were dissolved in 50 g of purified water precooled to below 5° C. Poloxamer was added portionwise to the solution with stirring to make a suspension. The suspension was stood at below 5° C. for 24 hours to become a clear solution (Solution A). After the mixture of preservatives suspended in propylene glycol was heated to be a clear solution (Solution B), it was added to the solution A with stirring to make a homogeneous solution and then purified water was added to make 100 g of gel. The conventional method was used for the filling process.

EXAMPLE 2

| Gel-Cream | |
|---|---|
| Micronomicin sulfate | 0.5 g |
| Solcoseryl | 5.0 g |
| Poloxamer | 20.0 g |
| Propylene glycol | 3.0 g |
| Cetearyl octanoate | 10.0 g |
| Methyl p-hydroxybenzoate | 0.15 g |

| Gel-Cream | |
|---|---|
| Propyl p-hydroxybenzoate | 0.02 g |
| Purified water | q.s. |

Micronomicin sulfate and Solcoseryl were dissolved in 50 g of purified water precooled to below 5° C. Poloxamer was added portionwise to the solution with stirring to make a suspension. The suspension was stood at below 5° C. for 24 hours to become a clear solution (Solution A). After the mixture of preservatives suspended in propylene glycol was heated to be a clear solution (Solution B), it was added to the solution A with stirring to make a homogeneous solution and cetearyl octanoate was added and emulsified with stirring to make 100 g of gel-cream.

Conventional method was used for the filling process.

EXAMPLE 3

| Topical liquid Solution I | |
|---|---|
| Micronomicin sulfate | 0.5 g |
| Solcoseryl | 5.0 g |
| Poloxamer | 8.0 g |
| Propylene glycol | 3.0 g |
| Methyl p-hydroxybenzoate | 0.18 g |
| Propyl p-hydroxybenzoate | 0.02 g |
| Purified water | q.s. |

Micronomicin sulfate and Solcoseryl were dissolved in 50 g of purified water precooled to below 5° C. Poloxamer was added portionwise to the solution with stirring to make a suspension. After the mixture of preservatives suspended propylene glycol was heated to be a clear solution, it was added to the suspension with stirring to make a homogeneous solution and purified water was added to make 100 g of topical liquid solution. Conventional method was used for the filling process.

EXAMPLE 4

| Topical liquid Solution II | |
|---|---|
| Micronomicin sulfate | 0.5 g |
| Solcoseryl | 5.0 g |
| Poloxamer | 8.0 g |

-continued

| Topical liquid Solution II | |
|---|---|
| Propylene glycol | 3.0 g |
| Ethanol | 3.0 g |
| Methyl p-hydroxybenzoate | 0.18 g |
| Propyl p-hydroxybenzoate | 0.02 g |
| Purified water | q.s. |

The same procedures as described in Example 3 were repeated for the preparation of 100 g of topical liquid solution using ethanol in place of some part of purified water to accelerate the formation of the liquid film after application. The procedures are as follows; Micronomicin sulfate, Solcoseryl and ethanol were dissolved in 50 g of purified water precooled to below 5° C. Poloxamer was added portionwise to the solution with stirring to make a suspension. After the mixture of preservatives suspended in propylene glycol was heated to be a clear solution, it was added to the suspension with stirring to make a homogeneous solution and purified water was added to make 100 g of topical liquid solution. Conventional method was used for the filling process.

COMPARATIVE EXAMPLE 1

Ointment

| Micronomicin sulfate | 0.5 g |
|---|---|
| Solcoseryl | 5.0 g |
| White vaseline | 70.64 g |
| Anhydrous lanolin | 17.66 g |
| Liquid paraffin | 6.0 g |
| Methyl p-hydroxybenzoate | 0.18 g |
| Propyl p-hydroxybenzoate | 0.02 g |

A mixture of white vaseline, anhydrous lanolin, liquid paraffin, methyl p-hydroxybenzoate and propyl p-hydroxybenzoate were heated in a vessel at 80°~85° C. to be a clear solution.

After mixing the solution homogeneously, the solution was cooled to 50° C. (Solution A). After micronomicin sulfate dissolved in Solcoseryl were added to Solution A, the further mixing results in 100 g of ointment. Conventional method was used for the filling process.

COMPARATIVE EXAMPLE 2

Cream

| Micronomicin sulfate | 0.5 g |
|---|---|
| Solcoseryl | 5.0 g |
| Wax | 6.7 g |
| Xantan gum | 0.3 g |
| Stearyl alcohol | 6.7 g |
| Liquid paraffin | 4.7 g |
| Octyldodesyl myristate | 6.0 g |
| Butylated hydroxyanisole | 0.05 g |
| Butylated hydroxytoluene | 0.05 g |
| Cyclodextrin solution | 1.0 g |
| Sodium citrate | 0.03 g |
| Propylene glycol | 3.3 g |
| Colloidal siliconedioxide | 0.5 g |
| Microcrystalline cellulose | 0.5 g |
| Polyethylene glycol monostearate | 2.0 g |
| Arlacel 165 | 1.0 g |
| Sodium edetate | 0.1 g |

-continued

| Simethicone | 0.5 g |
|---|---|
| Methyl p-hydroxybenzoate | 0.15 g |
| Propyl p-hydroxybenzoate | 0.05 g |
| Purified water | q.s. |

A mixture of wax, stearyl alcohol, arlacel 165, polyethylene glycol monostearate, propyl p-hydroxybenzoate, simethicone, butylated hydroxytoluene, butylated hydroxyanisole, octyldodesyl myristate, and liquid paraffin were heated and dissolved homogeneously at 75°~8020 C. in vacuum emulsifying system to be a solution (Solution A). Colloidal siliconedioxide, xantan gum, methyl p-hydroxybenzoate, and microcrystalline cellulose were heated at 75°~8020 C. in some amount of purified water and dissolved homogeneously to be a clear solution (Solution B). Solution B was added portionwise and emulsified to solution A in vacuum emulsifying system (Emulsion C). Micronomicin sulfate, propylene glycol, sodium edetate, liquid paraffin, and sodium citrate were added in some amount of purified water in a separate vessel and then dissolved homogeneously (Solution D).

Emulsion C was cooled to 50° C. after the emulsification was completed and Solution D were added to Emulsion C with mixing to make 100 g of cream.

TEST EXAMPLE 3

In vitro dissolution Test of micronomicin sulfate

To measure the rate of release of micronomicin sulfate from various formulations such as gel, gel-cream, topical liquid solution, ointment and cream which are produced in Example and Comparative Example, 1 loop of *Bacillus subtilis* ATCC 6633 was incubated in Muller Hinton Broth at 37° C. for 18 hours and then the culture broth was diluted to 1:100 with Muller Hinton Agar. The mixture was poured into a bioassay tray(245×245×20 mm) and solidified. Standard micronomicin sulfate solution and the above said formulation were loaded on the solidified media using paper disc (6 mm in diameter). After the media were placed at room temperature for 1 hour, the media were incubated at 37° C. for 18 hours and inhibitory diameter were measured. The released amount of micronomicin sulfate was calculated from the calibration curve of standard micronomicin sulfate, the results were shown in table 3.

TABLE 3

| Dosage form | No. of test | Release Rate of Micronomicin sulfate(%, mean ± S.D.) |
|---|---|---|
| Gel Example 1 | 5 | 98.5 ± 14.7 |
| Gel-Cream Example 2 | 5 | 95.1 ± 12.9 |
| Topical liquid Solution Example 3 | 5 | 100.7 ± 5.1 |
| Ointment Comparative Example 1 | 5 | 67.1 ± 10.2 |
| Cream Comparative Example 2 | 5 | 70.3 ± 8.8 |

Table 3 shows that the release rates of gel, gel-cream, and topical liquid solution are higher than those of cream or ointment. It is certified by these results that the gel, gel-cream, and topical liquid solution of the composition of the present invention are more desirable dosage forms.

TEST EXAMPLE 4

Stability test for dosage forms

To measure the stability from various formulations such as gel, gel-cream, topical liquid solution, ointment and cream which are produced in Example and Comparative Example, ointment, cream, gel and gel-cream are put into closed aluminium tube, and topical liquid solution is put into closed plastic vessel, and then those were placed at 40±1° C., 75±5% RH (Relative Humidity) for 6 months.

Micronomicin sulfate was analyzed by the experimental method of Micronomicin sulfate injection part in Specification and Assay method for antibiotics (Notice No. 1992–70 issued by Korea Ministry of Health and welfare) and Solcoseryl was analyzed by the experimental method of mixed L-threonin, sorbitol, valin, amino acid injection pan(Notice No. 85–9 issued by Korea National Institute of Health dated Oct. 10, 1985).

The results were shown in Table 4.

However, in the aspects of the economy of manufacture, dissolution of active ingredients, convenience in application, excellent adhesion, continuous effects of active ingredients, easiness in eliminating the film, more preferred is the gel form because it could increase the therapeutic effects by protecting wound from contaminates and humectant effect through the formation of a film on application as well as by major effect of active ingredients unlike the conventional ointments or creams. The topical liquid solution having both continuous therapeutic effect and convenience is more preferred than conventional cataplasma.

TEST EXAMPLE 5

Micronomicin sulfate elution test to ratio of carriers

For the various compositions with different content of poloxamer, sodium chloride, propylene glycol and cetearyl octanoate which were made by the same method in Example and Comparision Example, the rate of release of micronomicin sulfate and appearance were tested by the same method in Test Example 3. The results were shown in Table 5.

TABLE 4

| Dosage form | Components | Content (%) | | | |
|---|---|---|---|---|---|
| | | Starting | 2 months | 4 months | 6 months |
| Gel | Micronomicin sulfate | 100.4 | 99.9 | 100.8 | 99.8 |
| (Exam. 1) | Solco-Seryl | 101.9 | 100.8 | 102.8 | 101.1 |
| | aminoacetic acid L-Alanine | 102.0 | 101.5 | 101.7 | 101.4 |
| Gel-Cream | Micronomicin sulfate | 101.2 | 101.3 | 100.9 | 100.7 |
| (Exam. 2) | Solco-Seryl | 99.8 | 98.4 | 98.0 | 99.2 |
| | aminoacetic acid L-Alanine | 100.5 | 100.8 | 101.0 | 102.3 |
| Topical liquid solution | Micronomicin sulfate | 100.5 | 99.8 | 99.6 | 100.4 |
| | Solco-Seryl | 101.4 | 100.8 | 101.0 | 100.5 |
| (Exam. 3) | aminoacetic acid L-Alanine | 104.2 | 106.6 | 103.3 | 103.4 |
| Ointment | Micronomicin sulfate | 100.7 | 100.3 | 99.7 | 100.3 |
| (Com. | Solco-Seryl | 103.4 | 103.3 | 98.9 | 99.6 |
| Exam. 1) | aminoacetic acid L-Alanine | 100.4 | 100.2 | 100.0 | 100.6 |
| Cream | Micronomicin sulfate | 99.8 | 100.0 | 99.9 | 99.7 |
| (Com. | Solco-Seryl | 102.3 | 101.2 | 100.9 | 99.2 |
| Exam. 2) | aminoacetic acid L-Alanine | 101.6 | 101.2 | 99.6 | 100.3 |

The table 4 shows that the composition of the present invention have at least 3 years of the stability in gel, gel-cream, topical liquid solution, ointment, and cream.

TABLE 5

| Composition | Composition ratio of carriers (w/w %) | | | | Dosage form | Appearance | Release rate of Micronomicin sulfate (%) (mean ± SD) |
|---|---|---|---|---|---|---|---|
| | Poloxamer | Sod. chloride | Propylene glycol | Cetearyl octanoate | | | |
| Comp. 1 | 18 | 0.9 | 1 | — | Gel | Good | 99.2 ± 12.2 |
| Comp. 2 | 18 | 0.9 | 3 | — | Gel | Good | 98.5 ± 14.7 |
| Comp. 3 | 18 | 0.9 | 5 | — | Gel | Good | 99.8 ± 10.6 |
| Comp. 4 | 18 | 2.0 | 1 | — | Gel | Good | 98.1 ± 8.1 |
| Comp. 5 | 18 | 2.0 | 3 | — | Gel | Good | 99.3 ± 12.8 |

TABLE 5-continued

| Composition | Composition ratio of carriers (w/w %) Poloxamer | Sod. chloride | Propylene glycol | Cetearyl octanoate | Dosage form | Appearance | Release rate of Micronomicin sulfate (%) (mean ± SD) |
|---|---|---|---|---|---|---|---|
| Comp. 6  | 18 | 2.0 | 5 | — | Gel | Good | 99.6 ± 9.7 |
| Comp. 7  | 18 | 3.0 | 1 | — | Gel | Good | 97.8 ± 10.2 |
| Comp. 8  | 18 | 3.0 | 3 | — | Gel | Good | 95.1 ± 10.7 |
| Comp. 9  | 18 | 3.0 | 5 | — | Gel | Good | 96.2 ± 12.5 |
| Comp. 10 | 20 | 0.9 | 1 | — | Gel | Good | 94.2 ± 8.1 |
| Comp. 11 | 20 | 0.9 | 3 | — | Gel | Good | 95.3 ± 7.8 |
| Comp. 12 | 20 | 0.9 | 5 | — | Gel | Good | 96.7 ± 9.7 |
| Comp. 13 | 20 | 2.0 | 1 | — | Gel | Good | 94.2 ± 11.8 |
| Comp. 14 | 20 | 2.0 | 3 | — | Gel | Good | 92.8 ± 13.7 |
| Comp. 15 | 20 | 2.0 | 5 | — | Gel | Good | 93.2 ± 11.8 |
| Comp. 16 | 20 | 3.0 | 1 | — | Gel | Good | 93.8 ± 12.1 |
| Comp. 17 | 20 | 3.0 | 3 | — | Gel | Good | 94.7 ± 10.9 |
| Comp. 18 | 20 | 3.0 | 5 | — | Gel | Good | 95.1 ± 9.3 |
| Comp. 19 | 22 | 0.9 | 1 | — | Gel | Good | 92.7 ± 13.9 |
| Comp. 20 | 22 | 0.9 | 3 | — | Gel | Good | 91.9 ± 10.7 |
| Comp. 21 | 22 | 0.9 | 5 | — | Gel | Good | 90.8 ± 7.6 |
| Comp. 22 | 22 | 2.0 | 1 | — | Gel | Good | 93.7 ± 10.7 |
| Comp. 23 | 22 | 2.0 | 3 | — | Gel | Good | 91.8 ± 11.8 |
| Comp. 24 | 22 | 2.0 | 5 | — | Gel | Good | 90.9 ± 12.7 |
| Comp. 25 | 22 | 3.0 | 1 | — | Gel | Good | 92.3 ± 8.8 |
| Comp. 26 | 22 | 3.0 | 3 | — | Gel | Good | 94.2 ± 12.9 |
| Comp. 27 | 22 | 3.0 | 5 | — | Gel | Good | 90.1 ± 10.8 |
| Comp. 28 | 18 | — | 1 | 5  | G.C.[1] | Good | 96.8 ± 9.5 |
| Comp. 29 | 18 | — | 3 | 5  | G.C. | Good | 96.2 ± 11.7 |
| Comp. 30 | 18 | — | 1 | 10 | G.C. | Good | 95.8 ± 10.6 |
| Comp. 31 | 18 | — | 3 | 10 | G.C. | Good | 96.2 ± 9.7 |
| Comp. 32 | 18 | — | 1 | 15 | G.C. | Good | 96.7 ± 8.2 |
| Comp. 33 | 18 | — | 3 | 15 | G.C. | Good | 95.5 ± 11.7 |
| Comp. 34 | 20 | — | 1 | 5  | G.C. | Good | 93.8 ± 10.2 |
| Comp. 35 | 20 | — | 3 | 5  | G.C. | Good | 92.8 ± 11.2 |
| Comp. 36 | 20 | — | 1 | 10 | G.C. | Good | 95.7 ± 10.1 |
| Comp. 37 | 20 | — | 3 | 10 | G.C. | Good | 95.1 ± 12.9 |
| Comp. 38 | 20 | — | 1 | 15 | G.C. | Good | 94.8 ± 9.7 |
| Comp. 39 | 20 | — | 3 | 15 | G.C. | Good | 94.7 ± 11.6 |
| Comp. 40 | 22 | — | 1 | 5  | G.C. | Good | 93.8 ± 10.1 |
| Comp. 41 | 22 | — | 3 | 5  | G.C. | Good | 92.7 ± 10.1 |
| Comp. 42 | 22 | — | 1 | 10 | G.C. | Good | 92.5 ± 9.9 |
| Comp. 43 | 22 | — | 3 | 10 | G.C. | Good | 91.1 ± 12.1 |
| Comp. 44 | 22 | — | 1 | 15 | G.C. | Good | 90.2 ± 13.2 |
| Comp. 45 | 22 | — | 3 | 15 | G.C. | Good | 91.9 ± 10.1 |
| Comp. 46 | 5  | — | 1 | — | T.S.[2] | Good | 101.2 ± 7.3 |
| Comp. 47 | 5  | — | 3 | — | T.S. | Good | 102.7 ± 8.1 |
| Comp. 48 | 5  | — | 5 | — | T.S. | Good | 100.8 ± 8.7 |
| Comp. 49 | 8  | — | 1 | — | T.S. | Good | 99.7 ± 7.8 |
| Comp. 50 | 8  | — | 3 | — | T.S. | Good | 100.7 ± 5.1 |
| Comp. 51 | 8  | — | 5 | — | T.S. | Good | 100.5 ± 7.6 |
| Comp. 52 | 10 | — | 1 | — | T.S. | Good | 99.8 ± 6.1 |
| Comp. 53 | 10 | — | 3 | — | T.S. | Good | 101.7 ± 3.5 |
| Comp. 54 | 10 | — | 5 | — | T.S. | Good | 105.6 ± 10.2 |
| Comp. 55 | 12 | — | 1 | — | T.S. | Good | 101.8 ± 5.4 |
| Comp. 56 | 12 | — | 3 | — | T.S. | Good | 100.2 ± 6.2 |
| Comp. 57 | 12 | — | 5 | — | T.S. | Good | 103.1 ± 7.1 |
| Comp. 58 | 15 | — | 1 | — | T.S | Good | 101.8 ± 4.6 |
| Comp. 59 | 15 | — | 3 | — | T.S. | Good | 162.7 ± 5.1 |
| Comp. 60 | 15 | — | 5 | — | T.S. | Good | 101.3 ± 6.5 |

(1) G.C.: Gel-cream
(2) T.S.: Topical liquid solution

TEST EXAMPLE 6

Toxicity Study

1. Acute toxicity study
   1) Test article

The pharmaceutical composition consisted of deproteinized dialysate of calf's s blood and micronomicin sulfate at a ratio of 20:1 by weight.

2) Animals

Male and female SD rats of 9 weeks old

3) Test Article Preparation

Micronomicin sulfate was solubilized in the solution of deproteinized dialysate of calf's blood.

4) Method

Test animals were tasted for 18 hours, and then dose of 33 ml/kg of the test article preparation were administered subcutaneously at the dorsal area of the trunk of the test animals. The volume of treatment was calculated based on the body weight measured just before administration of test article. All animals were subjected to careful observation for any toxic symptoms or death for 7 consecutive days.

5) Results (1) Clinical Sign

After subcutaneous adminstration of test article at the dose of 33,200 mg/kg, all of the males(6 mice) and 5 females were dead. At the dose of 27,600 mg/kg, 5 males and all of the females were dead, and at the dose of 23,100 mg/kg, 3 mice of males and 3 mice of females were dead, and at the dose of 19,200 mg/kg, 1 mouse of male and 1 mouse of female were dead, respectively.

In the dead cases, activity and respiratory rate were decreased markedly. The time of occurance of death was within 24 hours. In the cases alive, decrease of activity and respiratory rate, saivation, tremor, and loss of consciousness were observed, occasionally. However, those animals recovered to normal state after 1 day of administration.

(2) Body Weight

There was no significant change in body weights by the test article treatment.

(3) Gross finding

There were no abnormal gross findings caused by test article.

Considering the above results of toxicity study by subcutaneous administration, there was no test article-related toxicity in general sign, body weight, and gross findings. $LD_{50}$ was estimated over 23,047 mg/kg. Therefore, the test article examined was considered to be very low toxic substance. The results were shown in table 6.

TABLE 6

Mortality of male and female SD rats treated subcutaneously with the composition of deproteinized dialysate of calf's blood and Micromicin sulfate.

| Sex | Dosage (mg/kg) | Days after treatment | | | | | | | | Final Mor-tality | $LD_{50}$ (mg/kg) |
|---|---|---|---|---|---|---|---|---|---|---|---|
| | | 0 | 1 | 2 | 3 | 4 | 5 | 6 | 7 | | |
| Male | 33,200 | 6 | — | — | — | — | — | — | — | 6/6 | 23,047.08 |
| | 27,600 | 5 | — | — | — | — | — | — | — | 5/6 | |
| | 23,100 | 3 | — | — | — | — | — | — | — | 3/6 | |
| | 19,200 | 1 | — | — | — | — | — | — | — | 1/6 | |
| | 16,000 | — | — | — | — | — | — | — | — | 0/6 | |
| | 0 | — | — | — | — | — | — | — | — | 0/6 | |
| Fe-male | 33,200 | 5 | — | — | — | — | — | — | — | 5/6 | 23,725.59 |
| | 27,600 | 6 | — | — | — | — | — | — | — | 6/6 | |
| | 23,100 | 3 | — | — | — | — | — | — | — | 3/6 | |
| | 19,200 | 1 | — | — | — | — | — | — | — | 1/6 | |
| | 16,000 | — | — | — | — | — | — | — | — | 0/6 | |
| | 0 | — | — | — | — | — | — | — | — | 0/6 | |

2. Subacute Toxicity Study

1) Test article

The pharmaceutical composition consisted of deproteinized dialysate of calf's blood and micronomicin sulfate at a ratio of 20:1 by weight.

2) Animals

Male and female SD rats of 5 weeks old

3) Test Article Preparation

Test article was dissolved in distilled water with various carriers to composition ratio.

4) Exposure Condition

Approximately 24 hours before the test, hair was removed from the dorsal area of the trunk of the animals by shaving. Test article was applied to the animals, uniformly over an area of 2.5×2.5 cm, once daily, for 30 days, at the doses of 1.97 g/kg, 3.94 g/kg, and 7.88 g/kg, respectively. For safety parameters, the examinations performed during treatment period were clinical signs, ophthalmology, body weights, food and water intakes.

After the observation period, all animals were subjected to necropsy. And gross findings, organ weight measurement, hematology, blood chemistry, urinalysis, and histopathology were followed.

5) Results

The following results were observed when test article was administered to SD rats, once daily, for 30 days, at the doses of 1.97 g/kg, 3.94 g/kg, and 7.88 g/kg, respectively.

(1) There was no test article-related change in clinical signs, body weight changes, and food and water intakes.

(2) There was no test article-related change in hematology, blood chemistry, and urinalysis.

(3) There was no test article-related abnormality in histopathological examination.

Considering the above results, no-effect level(NOVEL) was estimated over 7.88 g/kg under the condition of this study.

3. Skin Irritation Study

1) Test article

The pharmaceutical composition consisted of deproteinized dialysate of calf's blood and micronomicin sulfate at a ratio of 20:1 by weight.

2) Animals

Male New Zealand White rabbits, ranging between 1.3 kg and 1.8 kg of body weight.

3) Test Article Preparation

Test article was dissolved in distilled water with various carriers to compositon ratio.

4) Test Procedure

Approximately 24 hours before the test, hair was removed from the dorsal area of the trunk of the test animals by shaving. Four areas of skin were shaved in each animal and two areas were allocated to treated area. A dose of 0.5 g of the test article was applied to each area for 24 hours. After the end of exposure, residual test material was removed and all animals were examined for sings of erythema and edema, with scoring of the response according to Draize's method for 7 days.

5) Results

Observation of clinical signs and body weight measurement were performed following application of 0.5 g of test article for 24 hours.

(1) General Sign

There was no death or signs which seemed to be related to test article treatment during observation period of 24 hours when examined at 4 hour interval. All animals recovered to normal state without any delayed toxicity.

(2) Body Weights

The animals showed slight decrease of body weight on the first and the second day after treatment, but they were normalized thereafter without any problom. Therefore, this event would be slight effect caused by test material but was not considered to be the toxic effect.

(3) Skin Reaction

The primary irritation index was calculated as 0.35. Considering the above results, the test article examined could be graded as a slight irritating substance in rabbit model.

What is claimed is:

1. A pharmaceutical composition for skin disease, comprising 5–20 w/w % of deproteinized dialysate of calf's blood and 0.3–1 w/w % of aminoglycoside antibiotic as active ingredients and 18–22 w/w % of poloxamer, 1–5 w/w % of propylene glycol, and 0.5–3 w/w % of sodium chloride as gel-forming carriers.

2. The pharmaceutical composition according to claim 1, wherein the aminoglycoside antibiotic is selected from the group consisting of neomycin sulfate, gentamicin sulfate, micronomicin sulfate, amikacin sulfate, kanamycin sulfate, tobramycin sulfate, netilmicin sulfate, dibekacin sulfate, sisomicin sulfate and astromicin sulfate.

3. The pharmaceutical composition according to claim 2, wherein the aminoglycoside antibiotic is micronomicin sulfate.

4. The pharmaceutical composition according to claim 1, which is the gel-cream form containing 18~22 w/w % of poloxamer, 1~5 w/w % of propylene glycol and 5~15 w/w % of cetearyl octanoate as carriers.

5. The pharmaceutical composition according to claim 1, which is the topical liquid solution form containing 5~15 w/w % of poloxamer and 1~5 w/w % of propylene glycol as carriers.

* * * * *